US005487742A

United States Patent [19]

Cotrel

[11] Patent Number: 5,487,742

[45] Date of Patent: Jan. 30, 1996

[54] TRANSVERSE FIXATION DEVICE FOR A SPINAL OSTEOSYNTHESIS SYSTEM

[75] Inventor: Yves P. Cotrel, Paris, France

[73] Assignee: Sofamore Danek Group, Memphis, Tenn.

[21] Appl. No.: 158,156

[22] Filed: Nov. 24, 1993

Related U.S. Application Data

[63] Continuation of Ser. No. 666,665, Mar. 7, 1991, abandoned.

[30] Foreign Application Priority Data

Mar. 8, 1990 [FR] France .................................. 90 02970

[51] Int. Cl.[6] .................................................. A61F 5/00

[52] U.S. Cl. .................................................. 606/61

[58] Field of Search ................................ 606/61, 60, 72; 623/17, 16, 66

[56] References Cited

U.S. PATENT DOCUMENTS

| | | | |
|---|---|---|---|
| 2,187,642 | 1/1940 | Brown . | |
| 4,641,636 | 2/1987 | Cotrel | 606/61 |
| 4,815,453 | 3/1989 | Cotrel | 128/69 |
| 5,002,542 | 3/1991 | Frigg | 606/61 |
| 5,102,412 | 4/1992 | Rogozinski | 606/61 |
| 5,261,908 | 11/1993 | Campbell, Jr. | 606/61 |

FOREIGN PATENT DOCUMENTS

| | | | |
|---|---|---|---|
| 0348272 | 12/1989 | European Pat. Off. . | |
| 2244446 | 7/1975 | France . | |
| 2642642 | 8/1990 | France | 606/61 |
| 653799 | 4/1937 | Germany . | |

*Primary Examiner*—David Isabella
*Attorney, Agent, or Firm*—Woodard, Emhardt, Naughton, Moriarty & McNett

[57] ABSTRACT

This device comprises two fixation elements (4), each consisting of a hook (4) designed so as to be able to cover a rigid transverse bar (3) in a sliding manner and equipped with means (9, 8) for locking on the bar (3); this hook is made up of a body (5) and of two blades (6) spaced apart by a distance (d) of a width corresponding to that of the bar (3), and a span (7) for the hook to bear on the bar is made on the body (5) between the blades (6), which blades extend on each side of the bar when the hook straddles the latter. Two hooks (4), combined with a rectangular bar (3), form a relatively simple transverse connection device which can be positioned quickly and which has great torsional and flexural strength.

27 Claims, 3 Drawing Sheets

FIG. 1
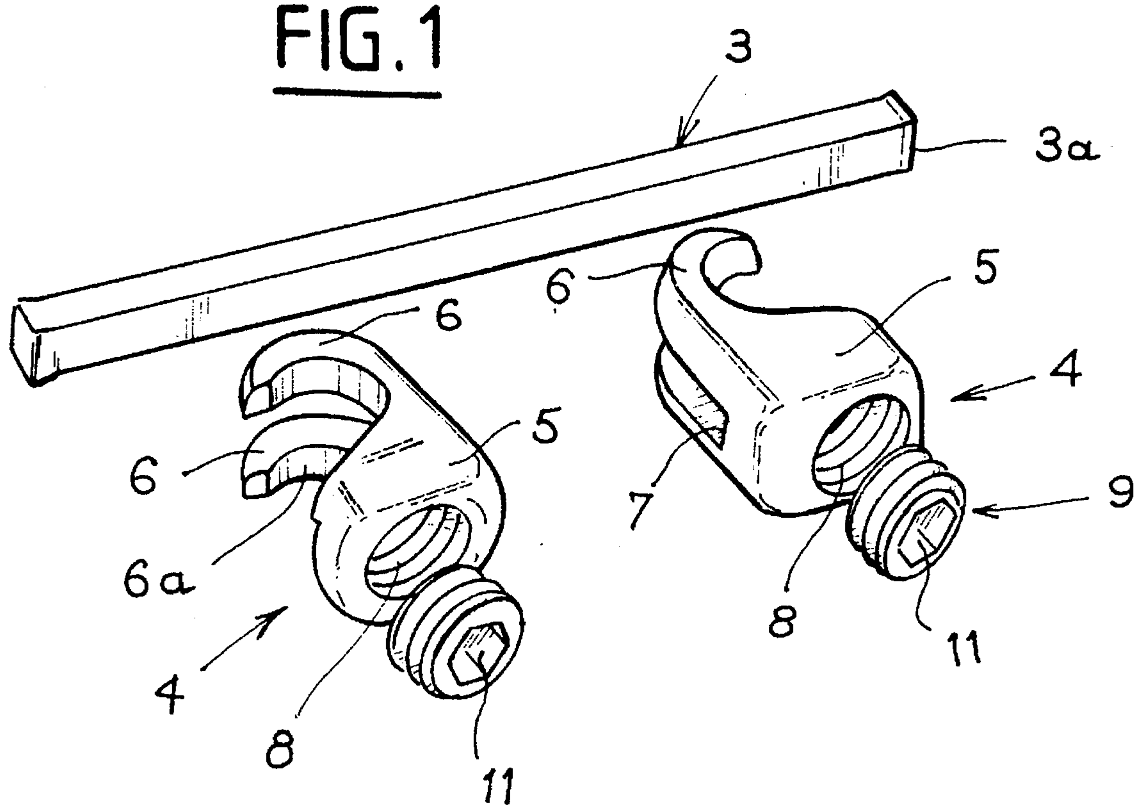
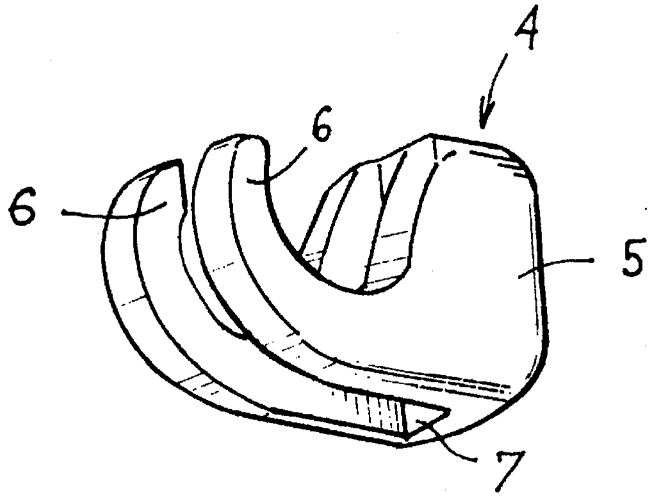
FIG. 2

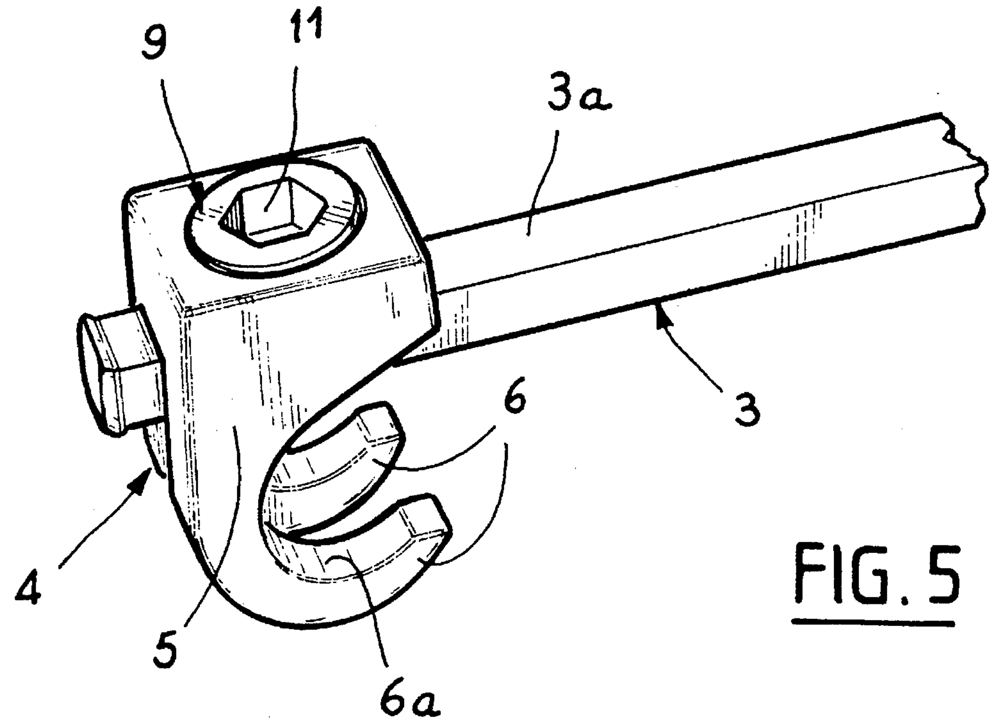
FIG. 5
FIG. 6
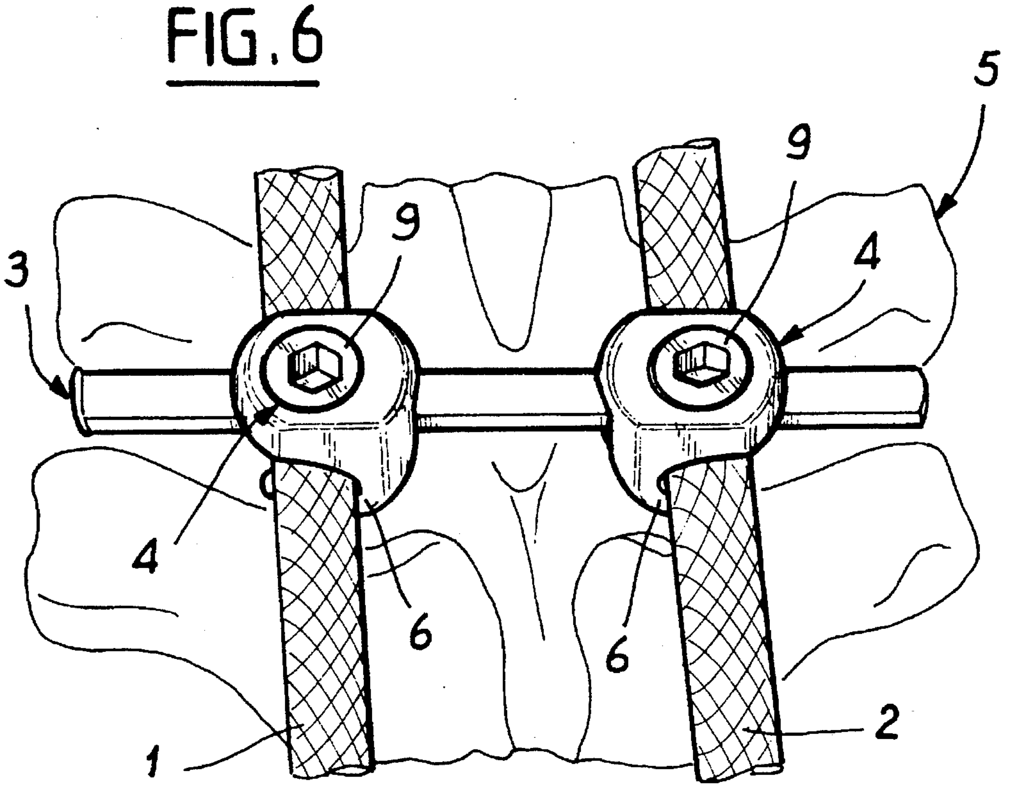

TRANSVERSE FIXATION DEVICE FOR A SPINAL OSTEOSYNTHESIS SYSTEM

This application is a continuation of application Ser. No. 07/666,665, filed Mar. 7, 1991, now abandoned.

The present invention relates to a fixation element for a transverse fixation device designed to ensure a rigid connection between two rods of a spinal osteosynthesis system, and to the transverse fixation device equipped with these elements.

It is known that in spinal osteosynthesis using the COTREL-DUBOUSSET technique, use is made of a transverse connection device (known by the abbreviation DTT), consisting of a fixed hook provided with a threaded rod, and of three free hooks which make it possible to bring together or space apart two knurled rods, by means of nuts and screws.

This system, necessary in order to guarantee the stability of the osteosynthesis equipment in the form of a frame, has the following disadvantages:

the time needed for its positioning is relatively long, its positioning is quite difficult, its torsional and flexural strength is relatively low.

The aim of the invention is therefore to overcome these disadvantages.

According to the invention, the fixation element consists of a hook designed so as to be able to cover, in a sliding manner, a rigid transverse bar and equipped with means for locking on said bar. This hook is made up of a body and two blades which are spaced apart by a distance of a width corresponding to that of the bar. A span for the hook to bear on the bar is made on the body between the blades, which blades extend on each side of the bar when the hook straddles the latter.

According to one feature of the invention, the two blades are curved in a radius of curvature corresponding to that of the rods, and thus designed so as to enclose the latter.

According to another characteristic, the span is planar in order to be able to bear on a planar surface of a bar of rectangular cross-section, the two blades extending parallel to one another on both sides of the said span.

The transverse fixation device, to which the invention also relates, comprises in combination a rigid bar of suitable length, and a pair of elements for fixation of the bar on the rods, such as mentioned hereinabove, being capable of being fixed in an adjustable manner at a chosen position on the bar.

This equipment is simplified compared to the equipment previously used and can therefore be positioned by the surgeon more quickly and more simply. In addition, it has a much greater torsional and flexural strength on account of the bar whose cross-section is considerable and constant over its entire length.

The invention will now be described with reference to the attached drawings which illustrate an embodiment thereof by way of a non-limiting example.

FIG. 1 is an exploded perspective view of an embodiment of the transverse fixation device according to the invention.

FIG. 2 is a perspective view, on an enlarged scale compared to FIG. 1, of one of the fixation elements of the device.

FIG. 5 is a partial elevation view of the bar of the device in FIGS. 1 to 4 straddled by a hook.

FIG. 6 is a perspective view of the transverse connection device according to FIGS. 1 to 5, positioned on a spinal segment.

The drawings show a transverse fixation device designed to ensure a rigid transverse connection between two rods 1 and 2 of a spinal osteosynthesis system which is to be positioned on a spinal segment S, which is shown partially in FIG. 6.

This device comprises, on the one hand, a rigid bar 3, cut to a suitable length, slightly greater than the space between the two rods 1 and 2, and a pair of fixation elements 4 which can be fixed in an adjustable manner at a chosen position on the bar 3. The latter has a suitable cross-section, for example rectangular.

Figure 3:
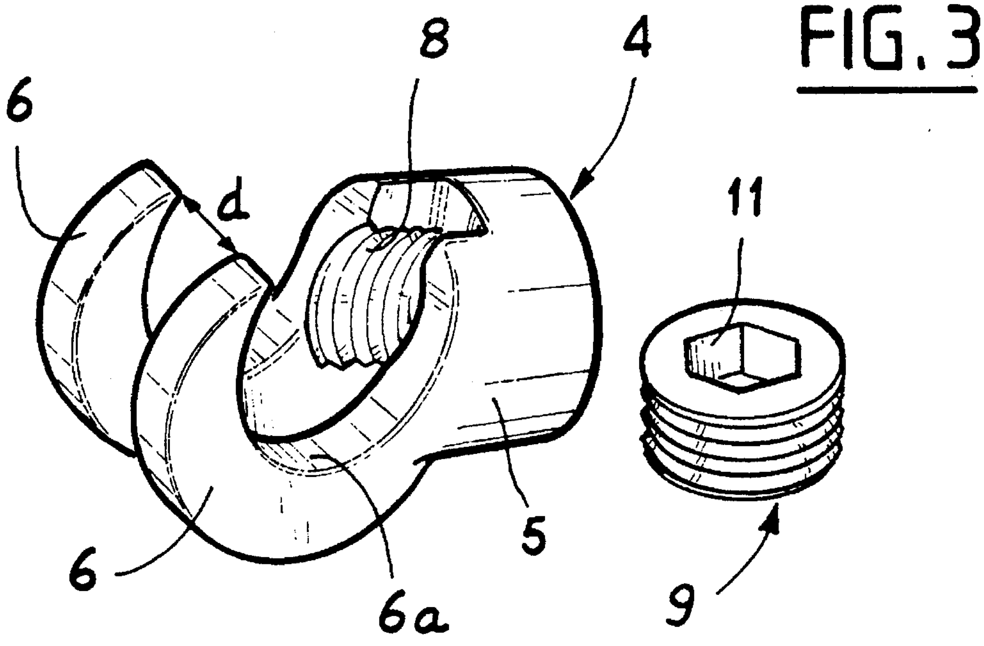
FIG. 3 is an exploded perspective view, at a different angle from FIGS. 1 and 2, of one of the hooks of the device, and of its plug for locking on the rod enclosed by this hook.
Figure 4:
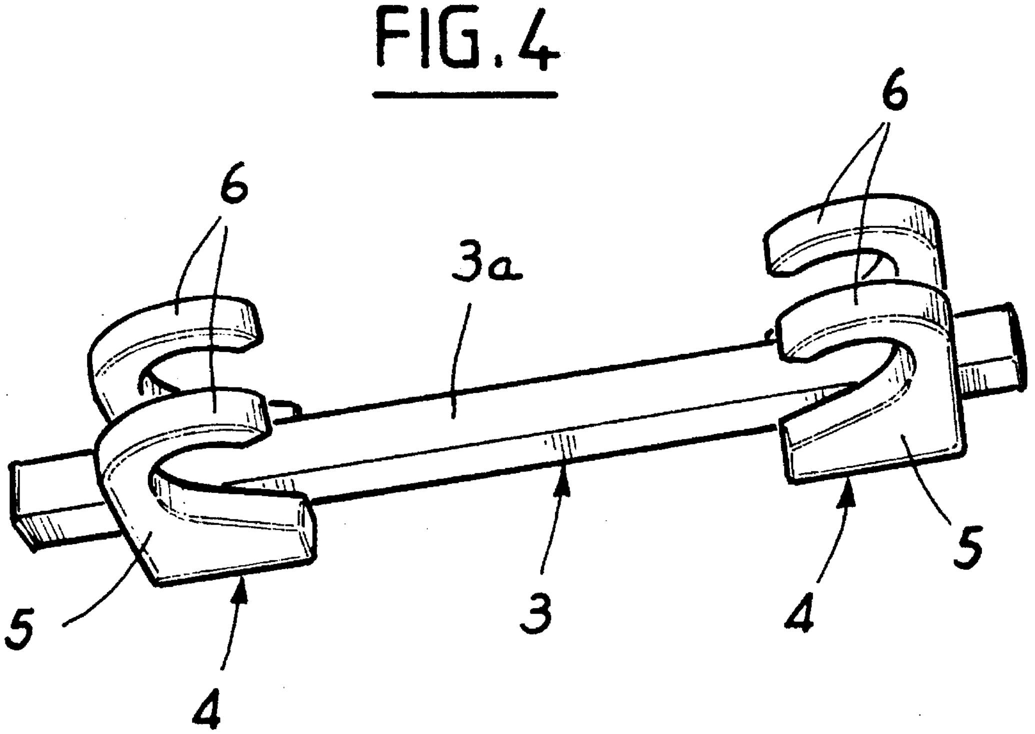
FIG. 4 is a perspective view of the device in FIGS. 1 to 3 when assembled, viewed from under the hooks, from the direction of the rods of the device.

Each element 4 consists of a hook designed so as to be able to cover the bar 3 in a sliding manner. To this end, each hook 4 comprises a body 5 and two blades 6 extending parallel to one another and separated by a distance d (FIG. 3) whose width corresponds to that of one of the surfaces **3*a* of the bar 3 of rectangular cross-section, in order to be able to straddle the bar by extending on both sides of the latter. The two blades 6 are curved in a radius of curvature corresponding to that of the knurled rods 1 and 2, in order to be able to enclose the latter in their bearing surfaces 6*a***, for example over slightly more than a half circumference.

Formed between the base of the two blades 6 and on the body 5 is a span 7 for the bearing of a surface **3*a* of the bar 3, this span 7 constituting the base of the seat of the bar in the hook 4. The span 7 extends from one end of the body 5 to the other, and in its central zone it is interrupted by a tapped hole 8 (FIGS. 1 and 3) formed in the body 5. A threaded plug 9 is designed to be able to be screwed into the corresponding tapped hole 8, in such a way that, at the end of screwing, it comes to bear on the surface 3*a* of the bar 3 placed in abutment on the span 7 and to lock the bar 3 by means of clamping between the plug 9 and the rod 1 (or 2). The surface for the bearing of the plug 9 on the bar 3 is planar or may optionally be provided with catching means, such as a point. In each plug 9, a profiled orifice 11 is made, for example a hexagonal socket, designed to receive a tool (not shown) for screwing of the plug 9**.

In order to position the device which has just been described, the surgeon places the bar 3 on the rods 1, 2 and then fits the two hooks 4 by making them straddle the bar 3 in order to enclose the rods 1, 2. Depending on the assembly chosen the hooks 4 are placed either for spacing the rods 1 and 2 (FIG. 6), or for bringing together these rods. In the spacing position, the blades 6 are oriented in opposite directions to one another, their base being situated between the rods 1 and 2. In contrast, in the position of bringing together, the hooks 4 are placed in such a way that their blades 6 are oriented towards one another, their base being situated to the outside of the rods 1 and 2.

The fixation of the bar 3 on the rods 1 and 2 is therefore carried out after the surgeon has spaced apart or brought together the two hooks 4, the center distance being maintained by tightening the screws or plugs 9 for locking the hooks 4 in their chosen position on the bar 3. The latter is then fixed relative to the two rods 1 and 2 and ensures the cohesion or stability of the osteosynthesis system, with great torsional and flexural strength.

The invention is not limited to the embodiment described and can comprise alternative embodiments. Thus, if desired, the cross-section of the bar 3 could be other than rectangular, and the plugs or screws 9 for locking of the hooks 4 can be replaced by any equivalent means.

I claim:

1. A spinal osteosynthesis system, comprising:

a spinal rod configured to be implanted on a spinal segment;

a transverse bar; and a fixation element including;

a body; and a bifurcated hook portion attached to said body, said hook portion defining two hook-shaped blades extending outwardly from said body and defining a first surface for engaging the rod, said blades being spaced apart along their outward extension a distance at least equal to a width of the transverse bar, and said body defining a second surface between said blades configured to slidingly engage a corresponding side of the transverse bar when the bar is fully seated between said blades.

2. The spinal osteosynthesis system of claim 1, wherein said outwardly extending hook-shaped blades curve in a radius corresponding to the radius of a spinal rod to slidingly enclose the rod when it is fully seated within the curvature.

3. The spinal osteosynthesis system of claim 1, further comprising:

a locking means for providing a rigid connection between the transverse bar and a spinal rod, said locking means including a threaded plug having a head portion at one end and a tip portion at an opposite end, said threaded plug configured for engagement in a corresponding tapped hole formed through said body, said tapped hole extending from said second surface of said body to an opposite surface of said body, so that when a transverse bar is fully seated between said blades of said fixation element and when a rod is enclosed within the curvature of the hook-shaped blades, said threaded plug may be screwed into said tapped hole until said tip portion of said threaded plug contacts the transverse bar and presses the transverse bar firmly against the enclosed rod, thereby locking the rod and transverse bar together in position.

4. A spinal osteosynthesis system, comprising:

a pair of spinal rods each configured to be implanted on a spinal segment;

a transverse fixation device, including, a rigid transverse bar, and a pair of fixation elements, each of said fixation elements including a body and a bifurcated hook portion, said hook portion defining two hook-shaped blades extending outwardly from said body for engaging the rod, said blades being spaced apart an equal distance from one another along their outward extension so that they are parallel and correspond to a width of said rigid transverse bar, and said body defining a planar surface between said blades configured to slidingly engage a corresponding planar side of said transverse bar when the bar is fully seated between said blades;

said transverse fixation device providing a rigid transverse connection between said rods when each of said fixation elements are engaged to the bar and a corresponding one of said rods.

5. The spinal osteosynthesis system of claim 4, further comprising:

a locking means for providing a rigid connection between the rigid transverse bar and a spinal rod, said locking means comprising a threaded plug having a head portion at one end and a tip portion at an opposite end, said threaded plug configured for engagement in a corresponding tapped hole formed through said body, said tapped hole extending from said planar surface to an opposite surface of said body, so that when a transverse bar is fully seated between said blades of said fixation element and when a rod is enclosed within the curvature of the hook-shaped blades, said threaded plug may be screwed into said tapped hole until said tip portion of said threaded plug contacts the transverse bar an presses the transverse bar firmly against the enclosed rod, thereby locking the rod and transverse bar together in position.

6. The spinal osteosynthesis system of claim 5, wherein said head portion of said threaded plug has a recess formed therein which is configured for receiving a screwing tool.

7. The spinal osteosynthesis system of claim 5, wherein said head portion and said tip portion of said threaded plug have the same cross-sectional diameter.

8. The spinal osteosynthesis system of claim 5, wherein said threaded plug is threaded along its entire length including said head portion of said threaded plug.

9. The spinal osteosynthesis system of claim 3, wherein said head portion of said threaded plug has a recess formed therein which is configured for receiving a screwing tool.

10. The spinal osteosynthesis system of claim 3, wherein said head portion and said tip portion of said threaded plug have the same cross-sectional diameter.

11. The spinal osteosynthesis system of claim 3, wherein said threaded plug is threaded along its entire length including said head portion of said threaded plug.

12. A spinal osteosynthesis system, comprising:

a first elongate member configured to be implanted on a spinal segment;

a second elongate member configured to be implanted on a spinal segment;

a transverse fixation device, including;

a body; and a bifurcated hook portion extending from said body, said hook portion defining two hook-shaped blades spaced apart to receive the first elongate member, said hook-shaped blades having a first bearing surface facing said body and configured to receive the second elongate member, wherein said body defines a second bearing surface spanning between said blades configured to receive the first elongate member such that the first elongate member is engageable between said second surface and the second elongate member.

13. The spinal osteosynthesis system of claim 12, in which the second elongate member is a spinal rod having a substantially circular cross-section, wherein said first surface of said hook-shaped blades is a curved surface to receive the circular rod.

14. The spinal osteosynthesis system of claim 12, in which the first elongate member is a bar having a planar face, wherein;

said second surface is planar; and said blades are spaced apart at said second bearing surface a distance at least equal to the width of the bar at said planar face.

15. The spinal osteosynthesis system of claim 12, further comprising:

a hole defined in said body and opening at said second bearing surface; and a plug engageable within said hole to extend from said opening and bear against the first elongate member to clamp the first elongate member against the second elongate member.

16. A spinal osteosynthesis system including a fixation element for connection between a spinal rod and a transverse bar of a transverse fixation device, said fixation element comprising:

a body; and a bifurcated hook portion attached to said body, said hook portion defining two hook-shaped blades extending outwardly from said body and defining a first surface for engaging the rod, said first surface configured to conform to a portion of an outer surface of the rod, said blades being spaced apart along their outward extension a distance at least equal to a width of the transverse bar, and said body defining a second surface between said blades configured to slidingly engage a corresponding side of the transverse bar when the bar is fully seated between said blades, said second surface configured to conform to a portion of an outer surface of the bar.

17. The spinal osteosynthesis system of claim 16, further comprising:

a hole defined in said body and opening at said second surface; and a plug engageable within said hole to extend from said opening and bear against the first elongate member to clamp the first elongate member against the second elongate member.

18. The spinal osteosynthesis system of claim 17, wherein said plug defines a recess, said recess configured for receiving a screwing tool.

19. The spinal osteosynthesis system of claim 17, wherein the portion of the outer surface of said transverse bar is planar;

said second surface is planar; and said blades are spaced apart at said second surface a distance at least equal to the width of the bar at the portion of the transverse bar.

20. A transverse fixation device for insuring a rigid transverse connection between two rods of a spinal osteosynthesis system, comprising in combination:

a rigid transverse bar, and a pair of fixation elements, each of said fixation elements including a body and a bifurcated hook portion, said hook portion defining two hook-shaped blades extending outwardly from said body and configured to conform to a portion of an outer surface of one of said rods, said blades being spaced apart an equal distance from one another along their outward extension so that they are parallel and correspond to a width of said rigid transverse bar, and said body defining a planar surface between said blades configured to slidingly engage a corresponding planar side of said transverse bar when the bar is fully seated between said blades.

21. The spinal osteosynthesis system of claim 20, further comprising:

a hole defined in said body and opening at said second surface; and a plug engageable within said hole to extend from said opening and bear against the first elongate member to clamp the first elongate member against the second elongate member.

22. The spinal osteosynthesis system of claim 21, wherein said plug defines a recess, said recess configured for receiving a screwing tool.

23. A transverse fixation device for connecting a first and a second elongate member of a osteosynthesis system, comprising:

a body; and a bifurcated hook portion extending from said body, said hook portion defining two hook-shaped blades spaced apart to receive the first elongate member, said hook-shaped blades having a first surface facing said body and configured to receive the second elongate member, said first surface configured to conform to a portion of an outer surface of the second elongate member; and wherein said body defines a second surface spanning between said blades configured to receive the first elongate member, said second surface configured to conform to a portion of an outer surface of the first elongate member such that the first elongate member is engageable between said second surface and the second elongate member.

24. The transverse fixation device of claim 23, in which the second elongate member is a spinal rod having a substantially circular cross-section, wherein said first surface of said hook-shaped blades is a curved surface to receive the circular rod.

25. The transverse fixation device of claim 23, in which the first elongate member is a bar having a planar face, wherein;

said second surface is planar; and said blades are spaced apart at said second surface a distance at least equal to the width of the bar at said planar face.

26. The transverse fixation device of claim 23, further comprising:

a hole defined in said body and opening at said second bearing surface; and a plug engageable within said hole to extend from said opening and bear against the first elongate member to clamp the first elongate member against the second elongate member.

27. The spinal osteosynthesis system of claim 23, wherein said plug defines a recess, said recess configured for receiving a screwing tool.

* * * * *